United States Patent [19]

Chung

[11] 4,147,716

[45] Apr. 3, 1979

[54] PREPARATION OF N-SUBSTITUTED CARBAMATES

[75] Inventor: Rack H. Chung, Stormville, N.Y.

[73] Assignee: BASF Wyandotte Corporation, Wyandotte, Mich.

[21] Appl. No.: 912,461

[22] Filed: Jun. 5, 1978

[51] Int. Cl.$^2$ .............................................. C07C 125/04
[52] U.S. Cl. ............................. 260/465 D; 260/453 P; 560/24; 560/32; 560/115; 560/157; 560/163
[58] Field of Search ............... 260/465 D; 560/24, 32, 560/115, 157

[56] References Cited

U.S. PATENT DOCUMENTS 2,647,916  8/1953  Kaiser ................................ 560/24

Primary Examiner—Dolph H. Torrence
Attorney, Agent, or Firm—Bernhard R. Swick; Robert E. Dunn; Samson B. Leavitt

[57] ABSTRACT

A method of preparing an N-substituted carbamate comprising reacting by heating in sulfolane at a temperature ranging from about 65° C. to about 100° C. (1) an alkali metal cyanate, (2) at least one sulfolane-soluble organic halide of the formula RX wherein X is halogen and R represents a radical selected from the group consisting of alkyl, alkenyl, aralkyl and aralkenyl, and (3) at least one sulfolane-soluble non-aromatic monohydric or polyhydric alcohol, and isolating the N-substituted carbamate thereby produced from the resulting reaction mass.

11 Claims, No Drawings

PREPARATION OF N-SUBSTITUTED CARBAMATES

This invention relates to a method of making N-substituted carbamates and more particularly to such a method involving alkali metal cyanates, organic halides and alcohols as reactants.

The production of N-substituted carbamates (carbamic acid esters) by addition of an alcohol to an isocyanate or by reaction of a chlorocarbonate with an amine is well known. Such methods are however not economical due to the relatively high cost of the isocyanate and amine reactants employed therein. Furthermore both the isocyanates and chlorocarbonates are highly toxic, their use thus necessitating special costly handling procedures for large scale industrial use. Some of the lower alkyl isocyanates are particularly hazardous because of their high volatility.

These handling difficulties can be overcome in some instances by generating the isocyanate in situ according to the method described in U.S. Pat. No. 2,647,916. This process involves heating a mixture of alkali metal cyanate, hydrocarbon halide, and an alcohol in the presence of a solvent at 100°-200° C. under atmospheric pressure or, preferably, under superatmospheric pressure. An excess of the alcohol reactant may serve as solvent, or other solvents selected from the group consisting of acetonitrile, propionitrile, β-methoxypropionitrile, dimethylcyanamide, acetone, dioxane, and nitrobenzene may be used.

While this process is said to work well with alcohols that are liquids at room temperature, it gives less satisfactory results with the higher molecular weight alcohols which are solids at or above room temperature. This is due to the poor solubility of the alkali metal cyanates in the reaction mass containing such higher boiling alcohols.

It is an object of this invention to provide a process which will not be subject to one or more of the above disadvantages. Another object of the invention is the provision of such a process which is operative regardless of whether the alcohol is a liquid or solid. Still another object of the invention is the provision of such a process operative with liquid or solid polyhydric alcohols, i.e. dihydric, trihydric, hexahydric alcohols and the like. A further object of the invention is the provision of such a process operative at relatively lower temperatures and/or pressures. Other objects and advantages will appear as the description proceeds.

The attainment of one or more of the above objects is made possible by this invention which includes a method of preparing an N-substituted carbamate comprising reacting by heating in sulfolane at a temperature ranging from about 65° C. to about 100° C. (1) an alkali metal cyanate, (2) at least one sulfolane-soluble organic halide of the formula RX wherein X is halogen and R represents a radical selected from the group consisting of alkyl, alkenyl, aralkyl and aralkenyl, and (3) at least one sulfolane-soluble non-aromatic monohydric or polyhydric alcohol, and isolating the N-substituted carbamate thereby produced from the resulting reaction mass.

According to a further feature of the invention, the above-described method is preferably carried out by adding the organic halide to a mixture of the alkali metal cyanate in sulfolane (tetrahydrothiophene-1,1-dioxide) within said temperature range to produce a sulfolane solution of the corresponding organic isocyanate of the formula RNCO, then adding the alcohol to said sulfolane solution, and then heating the resulting reaction medium within said temperature range until the reaction forming the desired N-substituted carbamate is completed. This sequential procedure facilitates more accurate control of the individual reactions between the cyanate and organic halide and between the isocyanate and the alcohol, and yields a purer product with less undesirable side products. According to a still further feature of the invention, when the alcohol is a solid at room temperatures up to about 100° C., it is added to the isocyanate sulfolane solution according to the above-described method in the form of its solution in a minimal amount of sulfolane, for example in concentrations corresponding to about 50% to 100% of saturation.

And according to yet a further feature of the invention, the N-substituted carbamate produced as described above is isolated from the completed reaction mass by cooling and mixing the mass with water, for example by drowning, whereby two layers are formed. The non-aqueous layer containing the carbamate is readily separated from the aqueous layer containing by-product alkali metal halide, as by decantation, siphoning, or draining or the like. This procedure substantially avoids decomposition and other by-products formed during recovery procedures involving distillation.

The operativeness and success in achieving the objects of this invention by use of sulfolane as the solvent reaction medium is surprising and unpredictable. Of a large number of solvent media tested, only sulfolane has been found uniquely effective for achieving the desired results. Among those solvents found to yield unsatisfactory results with solid alcohols are acetonitrile, dimethylformamide, dimethylsulfoxide, dioxane, diglyme, N-methylpyrrolidone, and tetrahydrofuran.

All the alkali metal cyanates, hydrocarbon halides and alcohols disclosed as reactants, all the equations disclosed for illustrating the manner in which such reactants yield the desired N-substituted carbamates, and the molar ratio of such reactants, in U.S. Pat. No. 2,647,916 are operative herein and such disclosures are accordingly incorporated herein by reference. The cyanates of lithium, rubidium, caesium, sodium and preferably potassium are operative. The halide X in the RX reactant may be chloride, iodide, fluoride or preferably bromide, and R may be aralkenyl, aralkyl, alkenyl (including cycloalkenyl) or alkyl (including cycloalkyl) of 1 to 20 or more carbon atoms such as octadecyl, preferably $C_{1-10}$ alkyl, more preferably $C_{2-4}$ alkyl, especially ethyl. The reactant RX reacts in equimolar proportions with the alkali metal cyanate of the formula MOCN, M being alkali metal, to yield, the corresponding isocyanate intermediate of the formula RNCO.

The alcohol reactant may be represented by the formula $R'(OH)_n$ wherein n is 1 to 6 or more and R' may include any of the values for R. For example, n is 1 in monohydric alcohols such as octadecanol, 2 in dihydric alcohols such as 1,4-butanediol and other glycols, 3 in trihydric alcohols such as glycerol, and 6 in hexahydric alcohols such as sorbitol. One mole of the isocynate RNCO reacts with (adds to) each —OH group in the alcohol to yield the corresponding carbamate group —OOCNHR. Accordingly, with the preferred monohydric alcohols, the reaction takes place between equimolar amounts of the alkali metal cyanate MOCN, the organic halide RX, and the alcohol R'OH. When a polyhydric alcohol reactant is employed (n is 2 to 6 or more), only sufficient molar proportions of the alkali metal cyanate and organic halide need be included to react with all or less than all of the —OH groups in the alcohol as desired. It will however be understood that an excess of any reactant over stoichiometric proportions may be included as desired and as influenced by the relative solubility, reactivity and/or cost of the individual reactants. Generally, when a monohydric alcohol is involved, molar proportions of alkali metal cyanate:organic halide:alcohol of, respectively, 1:1–2:0-.4–1 are preferred. When a polyhydric alcohol is involved, the indicated molar proportions of alcohol is divided by the number of —OH groups in the alcohol desired to be converted to carbamate.

Both R and R' in the organic halide and alcohol reactants may be chain-interrupted or substituted by substituents inert to the other reactants and the reactions in which they are involved. For example, a group of more complex alcohols, namely N-(2-hydroxyethyl) anilines, and including their derivatives containing $C_{1-2}$ alkyl, cyanoethyl or hydroxyethyl as another N substituent and/or at least one halo, nitro, cyanoethyl, hydroxyethyl, acetamino, $C_{1-2}$ alkyl or $C_{1-2}$ alkoxy as nuclear substituents, which are solid and soluble in sulfolane have been found effective for producing N-substituted carbamates which are useful as coupling components for coupling in known manner with diazotized aromatic amines such as p-methoxy-aniline, 2-methoxy-5-acetaminoaniline, 4-nitroaniline, 2,4-dinitroaniline, 4-chloroaniline, and the like to yield azo dyestuffs for coloring textiles having a basis of polyester, polyamide and/or polyacrylonitrile fibers and the like. The substituents in these complex hydroxyalkyl secondary and tertiary amino reactants are exemplary of those inert to the other reactants and the reactions in which they are employed in the process of this invention. Examples of such complex alcoholic reactants are:

N-(2-cyanoethyl)-N-(2-hydroxyethyl)aniline
N-(2-cyanoethyl)-N-(2-hydroxyethyl)-3-methylaniline
3-chloro-N-(2-cyanoethyl)-N-(2-hydroxyethyl)aniline
3-bromo-N-(2-cyanoethyl)-N-(2-hydroxyethyl)aniline
3-acetamino-N-(2-cyanoethyl)-N-(2-hydroxyethyl)aniline
5-acetamino-N-(2-cyanoethyl)-N-(2-hydroxyethyl)-2-methoxyaniline
5-acetamino-N-(2-cyanoethyl)-N-(2-hydroxyethyl)-2-ethoxyaniline
N,N-bis (2-hydroxyethyl)aniline
3-chloro-N,N-bis(2-hydroxyethyl)aniline
3-bromo-N,N-bis(2-hydroxyethyl)aniline
N,N-bis(2-hydroxyethyl)-3-methylaniline
3-acetamino-N,N-bis(2-hydroxyethyl)aniline
5-acetamino-N,N-bis(2-hydroxyethyl)-2-methoxyaniline
5-acetamino-2-ethoxy-N,N-bis(2-hydroxyethyl)aniline
N-(2-hydroxyethyl)aniline
3-chloro-N-(2-hydroxyethyl)aniline
3-bromo-N-(2-hydroxyethyl)aniline
N-(2-hydroxyethyl)-3-methylaniline
3-acetamino-N-(2-hydroxyethyl)aniline
5-acetamino-2-ethoxy-N-(2-hydroxyethyl)aniline
5-acetamino-N-(2-hydroxyethyl)-2-methoxyaniline
N-ethyl-N-(2-hydroxyethyl)aniline
3-chloro-N-ethyl-N-ethyl-N-(2-hydroxyethyl)aniline
3-bromo-N-ethyl-N-(2-hydroxyethyl)aniline
3-methyl-N-ethyl-N-(2-hydroxyethyl)aniline
3-acetamino-N-ethyl-N-(2-hydroxyethyl)aniline
5-acetamino-2-ethoxy-N-ethyl-N-(2-hydroxyethyl)aniline
5-acetamino-N-ethyl-N-(2-hydroxyethyl)-2-methoxyaniline In carrying out the process of this invention, the procedure described in U.S. Pat. No. 2,647,916 may be employed, namely effecting a simultaneous reaction between the selected molar proportions of the alkali metal cyanate, organic halide and non-aromatic alcohol reactants at a temperature ranging from about 65° C. to 100° C. in a sulfolane reaction medium. In such a procedure, a sufficient amount of sulfolane is employed to solubilize the organic halide reactant, the isocyanate intermediate, and the alcohol reactant, although it is preferred to employ a multiple of such amount to facilitate handling, control of temperature and/or reaction rates and the like. Typically, the amount by weight of sulfolane employed is about 4 to about 12 times the total weight of the alkali metal cyanate, organic halide and alcohol reactants. The reaction is preferably carried out with agitation at atmospheric pressures although superatmospheric pressures in a closed reaction vessel may be desirable in some instances, as for example when using highly volatile, low boiling reactants such as methyl and ethyl chlorides and fluorides and the like.

According to the preferred procedure, the alkali metal cyanate is first suspended in sulfolane, typically in a cyanate: sulfolane weight ratio of about 1:4–8, the suspension heated to about 65° to 100° C., and the organic halide added thereto with agitation preferably gradually or intermittently and preferably at a rate approximating its rate of reaction with the alkali metal cyanate to yield the corresponding organic isocyanate. If normally gaseous, the organic halide may be bubbled in below the surface of said suspension, and/or may be added in liquefied (cooled) form, the reaction vessel being closed and the contents preferably under superatmospheric pressure. If a liquid, the organic halide is added preferably dropwise or portionwise or injected below the surface of said suspension. If a solid, the organic halide may be added gradually or intermittently in particulate form (powder granules, etc.) or in the form of its solution in a minimal amount of sulfolane, for example in a concentration corresponding to about 50% to 100% of saturation. Typically, the addition of the organic halide takes place over a period of about 0.5 to about 3 hours.

To the resulting solution of organic isocyanate in sulfolane maintained in the indicated temperature range, the alcohol is added in bulk, gradually or intermittently as desired, with agitation. If a liquid, the alcohol is added neat (as such) in a manner like the above-described addition of organic halide. If a solid, the alcohol may be added in particulate form (powder, granules, etc.) or preferably in the form of its solution in a minimal amount of sulfolane, for example in a concentration corresponding to about 50% to 100% of saturation.

Following addition of the required amount of alcohol, the solution is then maintained in the indicated temperature range, preferably with agitation, until the reaction yielding the desired corresponding N-substituted carbamate is completed, typically for a period of about 1 to 5 hours. The carbamate product may if desired then be recovered from the resulting reaction mass by the distillation procedures described in U.S. Pat. No. 2,647,916.

Preferably, the resulting reaction mass is, preferably after cooling for example to below about 60° C. or to room temperature, mixed with water whereby a two layer liquid system is formed. The non-aqueous layer containing the carbamate product is readily separated, as by decantation, siphoning, draining or the like, from the aqueous layer containing the by-product alkali metal halide, and the product further purified if desired.

As indicated above, certain products of the process of this invention are useful as coupling components in the production of azo dyestuffs. Others are useful as E.P. lube oil additives, as described for example in U.S. Pat. No. 2,161,615. The products also find use as herbicides, plant growth regulants, and agricultural pesticides.

The following examples are only illustrative of preferred embodiments of the invention and are not to be regarded as limitative. All amounts and proportions referred to herein and in the appended claims are by weight unless otherwise indicated.

EXAMPLE 1

N-(2-cyanoethyl)-N-[2-(N-ethylcarbamoyloxy)ethyl]aniline

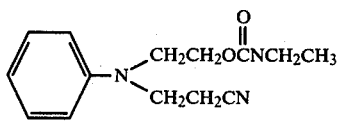

Into a 500 ml. three-necked round-bottomed flask equipped with thermometer, stirrer, reflux condenser, and dropping funnel are placed 40 g. (0.493 mole) of potassium cyanate and 250 ml. of sulfolane (tetrahydrothiophene-1,1-dioxide). This mixture is heated with stirring to 90° C. by means of an oil bath. Bromoethane (95 g., 0.8 mole) is then added dropwise to the mixture over a 1.5 hour period. The temperature of the reaction mixture drops to 75° C. during the addition of bromoethane. A solution of 50 g. (0.228 mole, 86.5%) N-(2-cyanoethyl)-N-(2-hydroxyethyl) aniline in 50 ml. of sulfolane is added, and heating of the resulting mixture is continued at 90° C. for three hours. The reaction mixture is cooled to room temperature and then poured into 2 liters of cold water. The mixture is agitated for 0.5 hour, and the two resulting layers separated. TLC of the organic layer in 4:1 benzene:acetone shows only a trace of starting material. The infrared spectrum of the product of the above formula shows absorptions at 3370, 2250, 1915, 1680, and 596 cm$^{-1}$.

EXAMPLE 2

This example describes the production of the product of Example 1 using chloroethane instead of bromoethane.

A mixture of 20.3 g. (0.25 mole) potassium cyanate and 125 ml. of sulfolane contained in a three-necked round-bottomed flask is heated to 90° C. by means of an oil bath. At this temperature 35 ml. (0.5 mole, 32.25 g.) chloroethane are added over a 2 hour period. During the addition the temperature of the reaction mixture drops to 78° C. After the addition of chloroethane is complete a solution of 27 g. (0.125 mole; 87% pure) N-(2-cyanoethyl)-N-(2-hydroxyethyl)aniline in 25 ml. sulfolane is added. The reaction mixture is heated for three more hours and then allowed to cool to room temperature. The cooled mixture is poured into water while stirring, and the resulting layers separated. TLC of the organic layer in 4:1 benzene: acetone shows that the reaction is incomplete probably due to loss of chloroethane by volatilization. Improved results call for use of a closed reaction vessel and/or superatmospheric pressure.

EXAMPLE 3

N-(2-cyanoethyl)-N-[2-(N-propylcarbamoyloxy)ethyl]aniline.

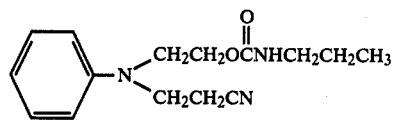

To a mixture of 4 g. (.05 mole) of potassium cyanate and 25 ml. of sulfolane at 90° C. are added dropwise 9 ml. (12.3 g, 0.1 mole) of 1-bromopropane over a one-hour period. After 10 minutes of stirring at the same temperature, a solution of 6 g. (0.027 mole) of N-(2-cyanoethyl)-N-(2-hydroxyethyl)aniline in 5 ml. sulfolane is added. The resulting mixture is stirred at 90°–100° C. for three hours and then allowed to cool to 50° C. The mixture is poured into 1 liter of water under agitation, and the resulting layers separated. TLC of the organic layer in 4:1 benzene: acetone shows the absence of starting alcohol with the product of the above formula.

This invention has been disclosed with respect to preferred embodiments thereof, and it will be understood that modifications and variations thereof obvious to those skilled in the art are to be included within the spirit and purview of this application and the scope of the appended claims. Mixtures of suitable organic halides and/or alcohols may be employed as, respectively, the organic halide reactant and/or the alcohol reactant.

What is claimed is:

1. A method of preparing an N-substituted carbamate comprising reacting by heating in sulfolane at a temperature ranging from about 65° C. to about 100° C. (1) an alkali metal cyanate, (2) at least one sulfolane-soluble organic halide of the formula RX wherein X is halogen and R represents a radical selected from the group consisting of alkyl, alkenyl, aralkyl and aralkenyl, and (3) at least one sulfolane-soluble non-aromatic monohydric or polyhydric alcohol, and isolating the N-substituted carbamate thereby produced from the resulting reaction mass.

2. A method as defined in claim 1 wherein the organic halide is added to a mixture of the alkali metal cyanate in sulfolane within said temperature range to produce a sulfolane solution of the corresponding organic isocyanate of the formula RNCO, the alcohol is then added to the said sulfolane solution, and the resulting reaction medium is then heated within said temperature range until the reaction forming the desired N-substituted carbamate is completed.

3. A method as defined in claim 2 wherein the alkali metal cyanate is potassium cyanate.

4. A method as defined in claim 3 wherein the organic halide is a $C_{1-10}$ alkyl halide.

5. A method as defined in claim 3 wherein the organic halide is a $C_{2-4}$ alkyl bromide.

6. A method as defined in claim 4 wherein the reaction takes place between about equimolar amounts of the alkali metal cyanate, organic halide and alcohol.

7. A method as defined in claim 6 wherein the alcohol is solid and is added in the form of its solution in sulfolane having a concentration corresponding to about 50% to 100% of saturation.

8. A method as defined in claim 7 wherein, in said mixture of alkali metal cyanate in sulfolane, the weight ratio of cyanate:sulfolane is about 1:4–8.

9. A method as defined in claim 8 wherein the N-substituted carbamate is isolated from said resulting reaction mass by mixing the mass with water and separating the resulting non-aqueous layer containing said carbamate from the aqueous layer containing by-product alkali metal halide.

10. A method as defined in claim 9 wherein the alcohol is an N-(2-hydroxyethyl) anilino compound.

11. A method as defined in claim 9 wherein the alcohol is N-(2-cyanoethyl)-N-(2-hydroxyethyl) aniline.

* * * * *